United States Patent
Changeux et al.

(10) Patent No.: US 6,252,132 B1
(45) Date of Patent: Jun. 26, 2001

(54) MUTANT MOUSE CONTAINING A KNOCKOUT MUTATION IN DNA ENCODING AN ENDOGENOUS ALPHA 4 SUBUNIT OF NICOTINIC ACETYLCHOLINE RECEPTOR

(75) Inventors: Jean-Pierre Changeux; Lisa Marubio, both of Paris (FR)

(73) Assignee: Institut Pasteur (FR)

( * ) Notice: Subject to any disclaimer, the term of this patent is extended or adjusted under 35 U.S.C. 154(b) by 0 days.

(21) Appl. No.: 09/427,581

(22) Filed: Oct. 27, 1999

Related U.S. Application Data
(60) Provisional application No. 60/106,691, filed on Nov. 2, 1998.

(51) Int. Cl.[7] .................. A01K 67/027; A01K 67/00; A01K 67/033; C12N 15/00
(52) U.S. Cl. .................. 800/18; 800/3; 800/8; 800/14; 800/18; 800/25; 435/320.1; 435/325; 435/455; 435/6; 536/23.4; 536/24.31
(58) Field of Search .................. 800/8, 3, 18, 14, 800/25; 514/225.8; 435/6, 320.1, 325, 455; 536/24.31, 23.4

(56) References Cited

FOREIGN PATENT DOCUMENTS
WO 94/20617    9/1994   (WO).
WO 96/03504    2/1996   (WO).

OTHER PUBLICATIONS
Bitner et al, 1998, J. Neurosci., 18(14): 5426–5432.*
Cordero–Erausquin et al, 1998, J Physiology Paris, 95(5–6): 423; Abstract from Meeting, Sep. 1–5, 1998.*
Decker et al, 1995, Euro. J. Pharmacol., 280: 79–89.*
Picciotto et al. 1995, Nature, 374: 65–67.*
Zoli et al, 1998, J Neurosci., 18(12): 4461–4472.*
Goldman et al, Cell. 1987, 48: 965–973.
Marubio, et al. "Reduced antinociception in mice lacking neuronal nicotinic receptor subunits" NATURE (April 1999) vol. 398, pp. 805–810.
Steinlein, et al. "Exon—Intron Structure of the Human Neuronal Nicontinic Acetylcholine Receptor α4 subunit (CHRNA4)" Genomics 32 (1996) PP. 289–294.
Orr–Urtreger et al. "Mice Deficient in the α7 Neuronal Nicotinic Acetylcholine Receptor Lack α–Bungarotoxin Binding Sties and Hippocampal Fast Nicotinic Currents" The Journal of Neuroscience (Dec. 1997) 17(23), pp. 9155–9171

* cited by examiner

*Primary Examiner*—Scott D. Priebe
*Assistant Examiner*—Peter Paras, Jr.
(74) *Attorney, Agent, or Firm*—Finnegan, Henderson, Farabow, Garrett & Dunner, L.L.P.

(57) ABSTRACT

A mutant mouse has germ cells and somatic cells containing a mutation comprising a disruption of the endogenous α4 subunit of the nicotinic acetylcholine receptor (nAChR) gene, wherein the disrupted α4 subunit of the nAChR gene results in the mouse lacking detectable levels of the endogenous α4 subunit of nAChR without a change in level of expression of other nAChR subunits as compared to a wild type mouse. The mutant mouse is useful for studying the roles of the various subunits of the nAChR. The results are useful in studying the antinociceptive, hypothermia, and locomotor effects of nicotine in other mammals.

7 Claims, 15 Drawing Sheets

CYTISINE BINDING

CONTROL KNOCK-OUT

MUTANT MOUSE CONTAINING A KNOCKOUT MUTATION IN DNA ENCODING AN ENDOGENOUS ALPHA 4 SUBUNIT OF NICOTINIC ACETYLCHOLINE RECEPTOR

CROSS-REFERENCE TO RELATED APPLICATION

This application is a Regular U.S. patent application based on U.S. Provisional application No. 60/106,691, filed Nov. 2, 1998, the entire disclosure of which is relied upon and incorporated by reference herein.

BACKGROUND OF THE INVENTION

This invention relates to a mutant mouse having a defect in an endogenous α4 subunit of the nicotinic acetylcholine receptor and to a transgenic animal based on the mutant mouse. In addition, this invention relates to isolated cells derived from these animals and to the use of the animals in assays for assessing the effects of nicotine and nicotinic agonists and antagonists in these animals and cells. Finally, this invention provides a nucleotide construct for use in generating these animals and cells.

The nicotinic acetylcholine receptor (nAChR) is a pentameric protein that forms a non-selective cation channel at the neuro-muscular junction and in the central nervous system (CNS). The genes encoding the neuronal nicotinic receptor subunits represent a large multigene family consisting of at least eight alpha subunits (α2–9) and three beta subunits (β2–4). Each subunit has four putative transmembrane-spanning domains (M1–4) and a similar topological structure.

Neuronal receptors form either heteropentamers comprised of a total of 5 subunits: Two alpha subunits (α2, α3, α4, or α6) and three beta subunits (β2 or β4) or they are capable of forming homopentamers (α7, α8 or α9) (Refs. 1 and 2). The binding site for acetylcholine (ACh) is found at the interface between α and β subunits indicating that both types of subunits contribute to the various pharmacological profiles of neuronal nAChRs (Ref. 3).

In situ hybridization experiments have shown the neuronal nAChR subunits to have diverse yet overlapping expression patterns in the CNS. β2 is the most widely expressed subunit in the peripheral nervous system (PNS), while α4 expression is almost as ubiquitous, but α4 is more limited to the CNS with only a small amount of expression seen in the PNS (Refs. 4 and 5). These findings have been further confirmed by immunoprecipitation experiments, which indicate that in vivo receptors in the CNS are primarily composed of α4 and β2 subunits (Ref. 6).

The pharmacology of the nAChRs has been extensively demonstrated with the Xenopus oocyte heterologous expression system (Ref. 7). This approach is limited, however, as the endogenous composition of nAChRs is still not known. While the rank order of potencies of nicotinic agonists seen in vivo more or less correspond to those observed in vitro, the single channel conductance of nAChR in vivo rarely coincides with the values found in Xenopus oocytes (Ref. 2).

Another approach to identify the composition of nAChR is to examine the nicotinic responses in knockout animals. This approach has been validated with the β2 nAChR subunit knockout mice where the β2 subunit was found to be necessary for a nicotine elicited response in the thalamus, but not in the medial habenula (Ref. 8). Furthermore, β2 was found to be a necessary component of the high affinity binding site for nicotine.

Moreover, certain behavioral effects of systemic nicotine are not clearly associated with the activation of particular structures. Nicotine has been demonstrated to act as an enhancer of memory and attention (Ref. 10), as an antinociceptive (Ref. 11), and as an anxiolytic (Ref. 12). The composition of the subunits of the nAChRs that mediate these responses are not known. On the other hand, the activation of nAChR by endogenous ACh in these different behaviors remains to be demonstrated. Thus, there exists a need in the art for a way to examine this contribution by comparison with wild type animals.

Further, because the precise roles of the various subunits of the nAChR are unknown at this time, there exists a need in the art for an animal model to study such roles. The generation of a mutant mouse having defective nAChR subunits would aid in defining the normal roles of the various subunits, and allow an animal model of nAChR deficiency to be used in the design and assessment of chemical approaches to regulating nicotine effects. Such a nAChR modified mutant or transgenic animal could also be used as a source of cells for cell culture.

SUMMARY OF THE INVENTION

This invention aids in fulfilling these needs in the art. More particularly, this invention provides a mutant mouse whose germ cells and somatic cells contain a mutation comprising a disruption of the endogenous α4 subunit of the nicotinic acetylcholine receptor (nAChR) gene. The disrupted α4 subunit of the nAChR gene results in the mouse lacking detectable levels of the endogenous α4 subunit of nAChR without a change in level of expression of other nAChR subunits as compared to a wild type mouse.

In one embodiment of the invention, the disruption can be introduced into the mouse or an ancestor of the mouse via homologous recombination in embryonic stem cells. In another embodiment, the mutation can be introduced into an ancestor of the mouse at an embryonic stage following microinjection of embryonic stem cells into a mouse cell.

In one embodiment, the mouse of the invention can be fertile and can transmit the mutation to its offspring. In another embodiment, the mutant mouse of the invention is post-natal.

The germ cells and somatic cells of the mutant mouse of the invention can additionally comprise a transgene within the disrupted α4 subunit of the nAChR. For instance, the transgene can encode a selectable marker. As examples, the transgene can encode neomycin resistance or diphtheria toxin.

Another embodiment of the invention comprises a mutant mouse homozygous for a disrupted α4 subunit of the mouse nicotinic acetylcholine receptor gene in the central nervous system of the mouse, wherein the receptor gene is disrupted by a selectable marker sequence introduced into the mouse or an ancestor of the mouse by homologous recombination at an embryonic stage. The disrupted α4 subunit of the nAChR gene results in the mouse having a reduced level of the α4 subunit of the nAChR without a change in level of expression of other nAChR subunits as compared to a wild type mouse.

An alternative embodiment of the invention provides a mutant mouse having α and β subunits of nAChR, wherein the mutant mouse is homozygous or heterozygous for a mutation in the α4 subunit of nAChR. The mutation has been introduced into the mouse or an ancestor of the mouse via homologous recombination in embryonic stem cells. The mouse does not express a functional mouse α4 nAChR subunit. In another embodiment of the invention, the mutant mouse does not express functional mouse α4 and β2 nAChR subunits.

In addition, the invention provides an isolated cell line derived from the mutant mouse of the invention. In one embodiment, a mouse embryonic stem (ES) cell line comprises a defective α4 subunit of mouse nicotinic acetylcholine receptor (nAChR), wherein the cell line lacks detectable levels of the α4 subunit of nAChR without a change in level of expression of other nAChR subunits as compared to ES cells from a wild type mouse.

Also, this invention provides an α4 subunit of mouse nicotinic acetylcholine receptor (nAChR) DNA knockout construct comprising a selectable marker sequence flanked by DNA sequences homologous to the α4 subunit of mouse nicotinic acetylcholine receptor gene, wherein when the construct can be introduced into a mouse or an ancestor of a mouse at an embryonic stage. The selectable marker sequence can disrupt the nAChR gene in the mouse and can result in the mouse having a reduced level of the α4 subunit of the nAChR without a change in level of expression of other nAChR subunits as compared to a wild type mouse. In one embodiment, the construct can comprise 5' to 3', the α4 subunit of the nAChR gene disrupted by a diphtheria toxin-A gene for selection against random integration, and the first 900 bp of exon 5 of the α4 subunit replaced by a gene encoding neomycin. This invention provides a vector comprising the α4 subunit of mouse nicotinic acetylcholine receptor DNA knockout construct.

Still further, this invention provides a method of screening for a compound that is an agonist or antagonist of nicotine. The method comprises:

(A) exposing a mutant mouse of the invention to the compound;

(B) administering nicotine to the mutant mouse prior to, after, or simultaneously with step (A); and (C) determining the response of the mutant mouse to the nicotine, wherein a change in response compared to an untreated mouse of the invention is indicative of the compound functioning to alter nicotinic activity.

The method of the invention can be carried out, for example, by determining the response by the tail-flick method, the hot plate method, or by nicotine induced hypothermia.

Mapping of the neuronal nicotinic receptors in brain slices from mice of the invention using tritiated nicotine revealed a complete loss of binding in all regions of the brain except for the interpeduncular nucleus where some binding remains. Tritiated epibatidine binding in brain slices from mice of the invention also disappears in homozygote mutant mice in most brain regions except for the interpeduncular nucleus, substantia nigra, superior colliculus, and medial habenula. No changes in $^{125}I$ α-bungarotoxin binding levels were observed. These results demonstrate that the α4 subunit is an important component of high activity nicotine and epibatidine binding sites in the brain.

Finally, on a behavioral level, mutant mice of the invention show a loss of nicotine-induced analgesia using the hot plate as a model. In contrast, there is a shift in the dose-response curve to nicotine using the tail-flick assay. This indicates that the α4 subunit is implicated in supra-spinal nicotine-induced analgesia and to a lesser extent in spinal nicotine-induced analgesia. Furthermore, this effect acts through a different mechanism than morphine, as both mutant and wild type littermates display morphine-induced analgesia in both the hot plate and tail flick tests.

In summary, the α4 knockout mice of the invention, which lack a large proportion of the neuronal nAChRs, will be useful in identifying nicotine induced responses mediated by the α4 receptor, which include, analgesic, addictive, seizure-inducing, anxiolytic, and cognitive enhancing effects. In addition, these mice will be useful in studying nicotinic agonists and other agents that target certain behaviors while avoiding others. Further, these mice will be instrumental in examining the role of high affinity nicotinic receptors in the diverse effects of nicotine.

BRIEF DESCRIPTION OF THE DRAWINGS

This invention will be described in greater detail by reference to the drawings in which:

FIG. 2 depicts α4 subunit expression in knockout mice of the invention as determined by in situ hybridization.

FIG. 3(A–B) shows autoradiography results of nicotinic agonist binding in brain sections from knockout mice of the invention.

FIG. 4(A–B) depicts the results of patch clamp recording in brain slices of knockout mice of the invention.

DETAILED DESCRIPTION OF THE INVENTION

Figure 1A:
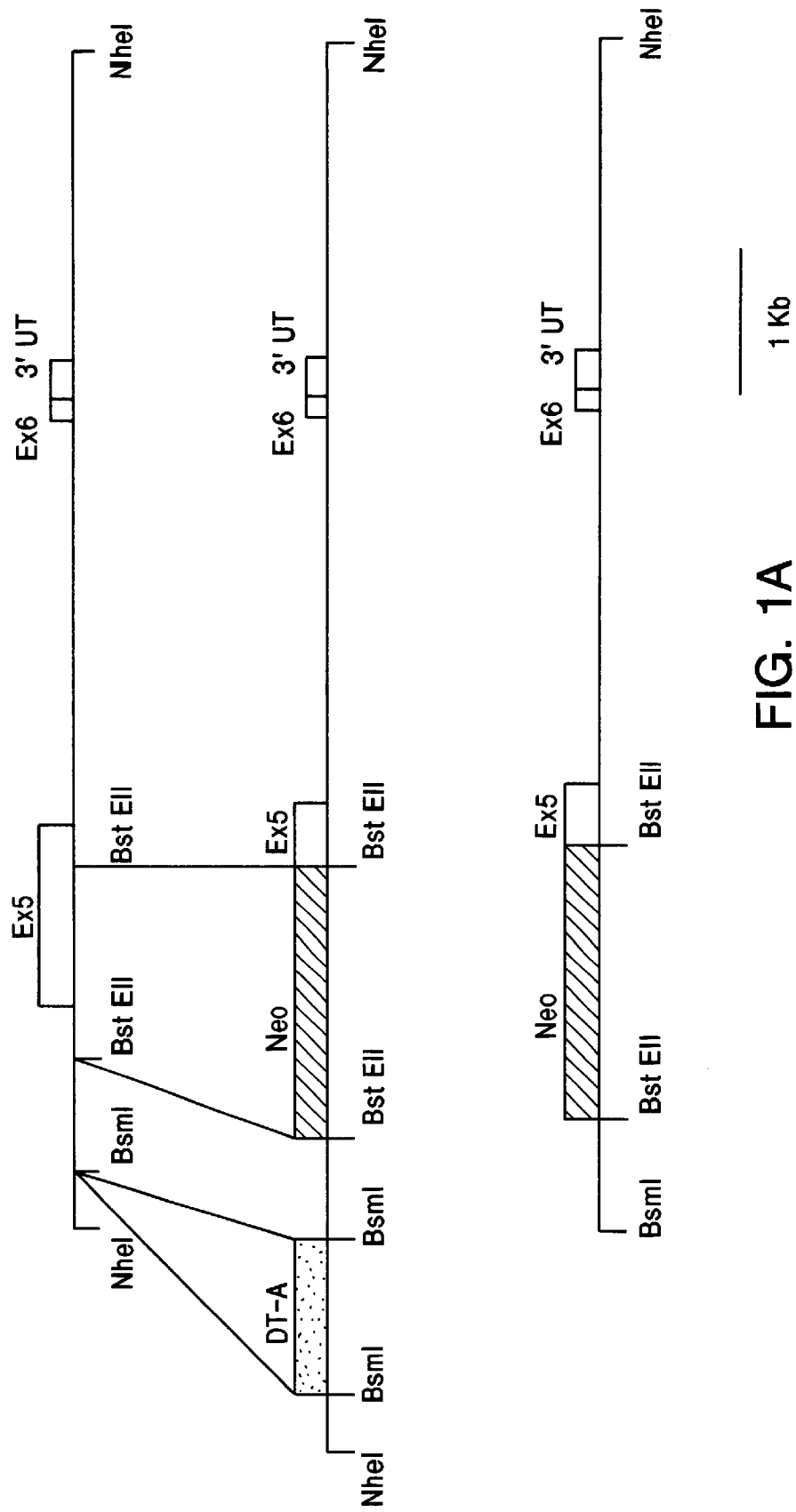
FIG. 1A describes a construct used to generate mice of the invention lacking a functional nicotinic receptor α4 subunit. Top, normal genomic structure of the mouse α4 gene. Middle, targeting replacement vector used to disrupt the endogenous α4 subunit gene. The first 900 bp of exon 5 were replaced by the gene encoding neomycin. Bottom, Structure of the mutated α4 gene.

Nicotine, a drug of addiction, has been shown to have wide-spread effects in the central nervous system (CNS) by binding to one or more of the numerous subtypes of nicotinic acetylcholine receptors (nAChR). However, the involvement of a particular subunit in pharmacology and behavior has been difficult to assess.

This invention provides a mutant line of mice, by gene targeting and homologous recombination, which lacks the neuronal α4 subunit of the nAChR, one of the most widely expressed subunits in the CNS. Mutant mice develop normally, are capable of reproduction, and are indistinguishable from their wild type littermates in a cage. α4 subunit mRNA was shown to be absent in mutant mice; however, no changes in the level of expression of other subunits is observed.

Using antibodies which have been obtained from Santa Cruz Biotechnologies Inc., Calif., directed against a peptide sequence RAVEGVQYIADHLKAEDTDF in the cytoplasmic loop of the α4 nAChR subunit, a complete loss of α4-like immunoreactivity is observed using both Western blotting and immunohistochemical techniques. $^3$H-nicotine and $^3$H-Cytisine binding sites are absent in most brain regions of mutant mice; however, some binding does remain in the interpeduncular nucleus. Furthermore, most $^3$H-epibatidine binding sites disappear in mutant mice, however, some binding is still observed in the interpeduncular nucleus, the superior colliculus, the medial habenula, and the substantia nigra.

In addition, electrophysiological recordings from brain slices reveal a marked loss of nicotine induced currents in the thalamus and substantia nigra pars compacta in mutant mice. On a behavioral level, mutant mice show a loss of the analgesic effect of nicotine using the hot plate model.

More particularly, by gene targeting and homologous recombination, we have mutated the α4 neuronal nAChR in mice of the 129 strain. Exon 5 of the mouse α4 nAChR was cloned by screening a γDASH II male 129 mouse strain genomic library with a full-length rat α4 clone. Six overlapping clones were found. Clone 1 was mapped by restriction enzyme digest (FIG. 1). The α4 nAChR subunit genomic clone encoding the intron 4,5,6 and the exons 5+6 designated α4 nAChR gene—NheI has been deposited at CNCM (Collection Nationale de Cultures de Microorganisms) on Oct. 30, 1998, under the number I-2088. Exon 5 of the genomic clone was fully sequenced and shown to be 82% identical to the human α4 nAChR in a 1380 base pair overlap at the nucleic acid level and 81% identical at the amino acid level. In its entirety, mouse α4 is most identical to human α4 in the transmembrane spanning domains and the amino acids known to contribute to the acetylcholine and nicotine binding sites. A targeting construct was designed by excising the majority of exon 5 and a portion of the upstream intron between two BstEII restriction digest sites. A cassette encoding neomycin resistance was inserted, and 0.9 KB further upstream the diphtheria toxin-A gene was inserted to select against random integration (FIG. 1). Embryonic stem cells were cultured as previously described (Picciotto et al., 1995) and transfected by electroporation with the linearized construct. Homologous recombination was initially detected by neomycin resistance and the polymerase chain reaction using a sense primer designed against a region in intron 4 that was not included in the construct and an anti-sense primer designed against the neomycin resistance gene in the construct. Four positive cell colonies were identified and subsequently injected into 3.5 day-old blastocysts from C57B1/6 mice. These injected blastocysts were then implanted in the uterus of a pseudopregnant mouse. Thirteen chimeric mice were subsequently born and when mature, bred with C57B1/6 mice. Two of these mice were able to transmit the 129 ES cells and 4 agouti mice out of about 500 black mice were born. One of these agouti mice contained the α4 mutation and was used for further crossing with C57B1/6 mice.

Various terms are used throughout this specification. The term "knockout" refers to partial or complete reduction of the expression of at least a portion of a polypeptide encoded by an endogenous gene, such as the α4 or β2 subunit of the nAChR of a single cell, selected cells, or all of the cells of a mammal, as compared to a wild type animal. The mammal may be a "heterozygous knockout",wherein one allele of the endogenous gene has been disrupted. Alternatively, the mammal may be a "homozygous knockout",wherein both alleles of the endogenous gene have been disrupted. The mutation may, without limitation, be an insertion, deletion, frameshift mutation, or a missense mutation. Preferably, the mutation is an insertion or deletion as described herein, or is a frameshift mutation that creates a stop codon.

The term "knockout construct" refers to a nucleotide sequence that is designed to decrease or suppress expression of a polypeptide encoded by an endogenous gene in one or more cells of a mammal. The nucleotide sequence used as the knockout construct is typically comprised of (1) DNA from some portion of the endogenous gene (one or more exon sequences, intron sequences, and/or promoter sequences) to be suppressed and (2) a marker sequence used to detect the presence of the knockout construct in the cell. The knockout construct can be inserted into a cell containing the endogenous gene to be knocked out. The knockout construct can then integrate with one or both alleles of the endogenous gene, e.g., the α4 subunit of nAChR, and such integration of the knockout construct can prevent or interrupt transcription of the full-length endogenous gene. Integration of the knockout construct into the cellular chromosomal DNA is typically accomplished via homologous recombination (i.e., regions of the knockout construct that are homologous or complementary to endogenous DNA sequences can hybridize to each other when the knockout construct is inserted into the cell; these regions can then recombine so that the knockout construct is incorporated into the corresponding position of the endogenous DNA).

Typically, the knockout construct is inserted into an undifferentiated cell termed an embryonic stem cell (ES cell). ES cells are usually derived from an embryo or blastocyst of the same species as the developing embryo into which it can be introduced, as discussed below.

By "transgenic" is meant any mammal that includes a nucleic acid sequence, which is inserted into a cell and becomes a part of the genome of the animal that develops from that cell. Such a transgene may be partly or entirely heterologous to the transgenic animal.

Thus, for example, substitution of the naturally occurring α2 subunit gene for a gene from a second species results in an animal that produces the receptor of the second species. Substitution of the naturally occurring gene for a gene having a mutation results in an animal that produces the mutated receptor. A transgenic mouse carrying the human α4 subunit receptor can be generated by direct replacement of the mouse α4 subunit with the human gene. These transgenic animals are critical for drug antagonist studies on animal models for human diseases, and for eventual treatment of disorders or diseases associated with nicotine responses. Other examples of nucleic acid sequences that can be inserted into the defective α4 subunit of the nAChR in mutant animals of the invention to provide a transgenic animal are mutated forms of α4. Recently, α4 has been linked to autosomal dominant nocturnal frontal lobe epilepsy in humans. Two mutations in or near the M2 region, which lines the channel fore, has been identified in two separate families. (Ref. 13-Ref. 14). Transgenic mice carrying these mutations will be extremely useful in studying this disease.

Transgenic nAChR animals are useful in characterizing the in vivo activity of modulators of nicotine activity. A transgenic animal carrying a "knockout" of nAChR subunit, such as α4 or α4 and β2, is useful for the establishment of a nonhuman model for diseases involving such receptors, and to distinguish between the activities of the different nicotinic receptors in an in vivo system.

Although mutant mice represent a preferred embodiment of the invention, other transgenic mammals, including without limitation, mutant rodents (for example, hamsters, guinea pigs, rabbits, and rats), and mutant pigs, cattle sheep, and goats can be constructed by standard techniques and are included within the scope of this invention. The terms "rodent" refers to all members of the phylogenetic order Rodentia, including any and all progeny of all future generations derived therefrom. The term "murine" refers to any and all members of the family Muridae, including without limitation, rats and mice.

The term "progeny" refers to any and all future generations derived or descending from a particular mammal, i.e., a mammal containing one or more knockout constructs inserted into its genomic DNA, whether the mammal is heterozygous or homozygous for the knockout construct. Progeny of any successive generation are included herein, such that the progeny, the F1, F2, F3 generations, and so on indefinitely containing the knockout construct are included in this definition.

Included within the scope of this invention is a mammal in which one or both nAChR α4 subunit alleles, as well as one or both alleles of another gene(s), have been knocked out. Such a mammal can be generated by repeating the procedures set forth herein for generating an nAChR α4 subunit knockout mammal but using another gene, or by breeding two mammals, one with one or both alleles of nAChR α4 subunit knockout mammal but using another gene, or by breeding two mammals, one with one or both alleles of α4 subunit knocked out, and one with one or both alleles of a second gene knocked out, to each other, and screening for those offspring that have the double knockout genotype (whether a double heterozygous or a double homozygous knockout genotype, or a variation thereof.

Transgenic animals that express a defective α4 subunit of nAChR may be used to obtain animals with additional phenotypes, e.g., phenotypes associated with a disease. This is accomplished by combining the different genotypes of different animals by cross-breeding the animals containing the different genotypes or by integrating an appropriate transgene into a zygote or ES cell of an animal.

At this stage, two breeding schemes for proliferation of the mutant mice have been developed. Using C57B1/6 mice, a backcross has been started to obtain a genetically pure line of mice. In addition, heterozygote mice have been crossed together to obtain both wild type and homozygous mutant mice. The genotype of each mouse can be identified using PCR with a set of primers directed against the neomycin resistance gene and another set directed against exon 5 of the α4 subunit of the nAChR.

The phrases "disruption of the gene","gene disruption",or simply "disruption",refer to insertion of a nAChR α4 subunit nucleotide sequence knockout construct into a homologous region of the coding region of the endogenous nAChR α4 subunit gene (usually containing one or more exons) and/or the promoter region of this gene so as to decrease or prevent expression of the full length nAChR α4 subunit in the cell. Insertion is usually accomplished by homologous recombination. By way of example, a nucleotide sequence knockout construct can be prepared by inserting a nucleotide sequence comprising an antibiotic resistance gene into a portion of an isolated nucleotide sequence encoding the nAChR α4 subunit that is to be disrupted. When this knockout construct is then inserted into an embryonic stem cell ("ES cell"), the construct can integrate into the genomic DNA of at least one nAChR α4 subunit allele. Thus, many progeny of the cell will no longer express nAChR α4 subunit at least in some cells, or will express it at a decreased level and/or in a truncated form, as at least part of the endogenous coding region of nAChR α4 subunit is now disrupted by the antibiotic resistance gene.

The term "marker sequence" refers to a nucleotide sequence that is (1) used as part of a larger nucleotide sequence construct (i.e., the "knockout construct") to disrupt the expression of the nAChR α4 subunit and (2) used as a means to identify those cells that have incorporated the nAChR α4 subunit knockout construct into the chromosomal DNA. The marker sequence may be any sequence that serves these purposes, although typically it will be a sequence encoding a protein that confers a detectable trait on the cell, such as an antibiotic resistance gene or an assayable enzyme not naturally found in the cell. The marker sequence can also typically contain either a homologous or heterologous promoter that regulates its expression.

By "regulatory region" is meant a sequence that is minimally necessary for direction of transcription and, if appropriate, translation of an associated nucleic acid coding sequence. The term includes auxiliary sequences that mediate gene expression in response to an external or internal stimulus, for example, expression that is inducible (for example, by temperature or a chemical stimulus), or expression that is tissue-specific (for example, nervous system-specific), or developmental stage-specific. "Regulatory region" sequences are generally located 5' (or "upstream") of the nucleic acid coding sequence, but may be located within or 3' (or "downstream") of the coding sequence.

FIG. 1 describes a construct used to generate knockout mice of the invention lacking the nicotinic receptor α4 subunit. FIG. 1A describes disruption of the gene encoding the α4 subunit of the nAChR. In the top of the FIG., the normal genomic structure of the mouse α4 gene is shown. In the middle, the targeting replacement vector used to disrupt the endogenous α4 subunit gene is shown. The diphtheria toxin-A gene (DTA) was used to select against random integration. The first 900 bp of exon 5 were replaced by the gene encoding neomycin. In the bottom of FIG. 1A, the structure of the mutated α4 gene is shown. Restriction sites BE, BstEII; R, EcoRI; B, BsmI; N, NheI are shown in the figure.

Figure 1B:
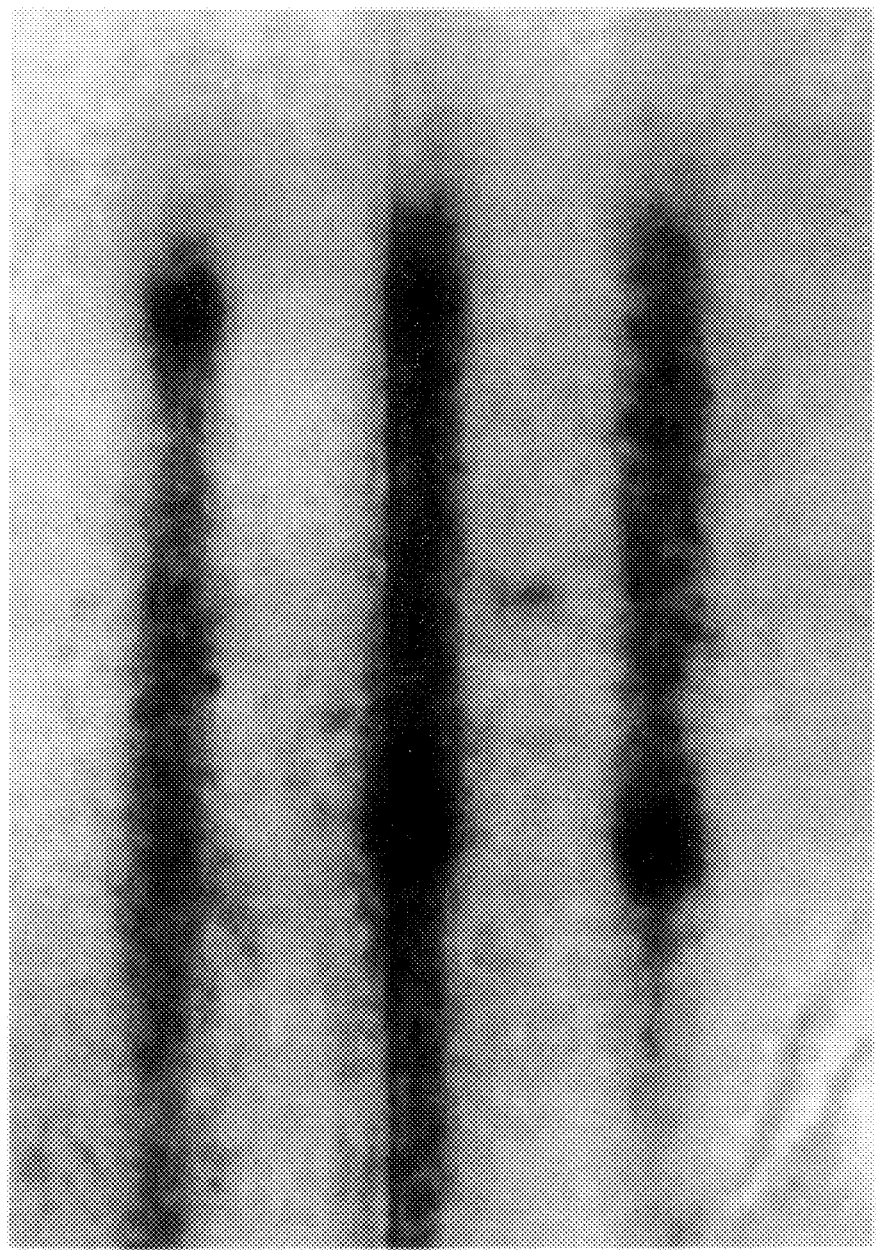
FIG. 1B shows the results of Southern blot analysis confirming homologous recombination.

Confirmation of homologous recombination was made by Southern blot analysis, and the results are shown in FIG. 1B. Lung genomic DNA from wild type, heterozygote, and knockout mice was restricted with EcoRI and hybridized with a radiolabelled probe from exon 5. A band of about 10 Kb indicates the presence of the wild type gene, while a band of 4.2 Kb indicates the presence of the mutated gene.

Figure 2A:
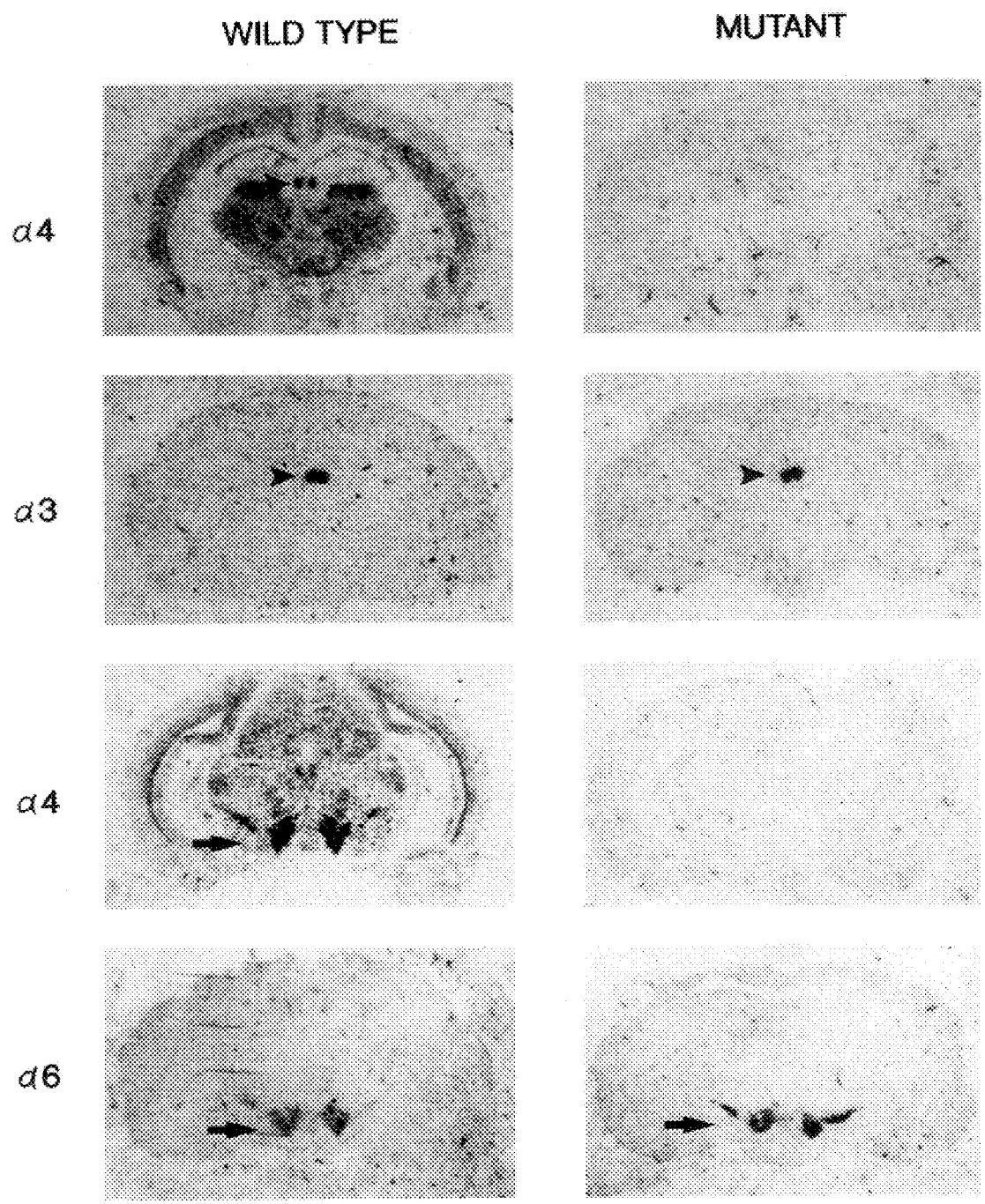
FIG. 2A describes mapping of neuronal nAChRs in mouse brain using in situ hybridization.

FIG. 2 depicts α4 subunit expression in knock-out mice as determined by in situ hybridization. FIG. 2A describes mapping of neuronal nAChRs in mouse brain using in situ hybridization.

Antisense oligonucleotide probes based on the cDNA sequences encoding α4,α3, and α6 subunits of the nAChR were used to detect their respective mRNA levels in serial sections from the brains of α4 +/+, +/−, and −/− mice. The upper panels shown midthalamic sections (bregma −1.5); arrowheads designate the medial habenula. The lower panels show mesencephalic sections (bregma −3.2); arrows designate the dopaminergic neurons of the ventral mesencephalon. α4 mRNA levels drastically diminish in –/– mice; however, there is no change in the expression of α5, α7, β2, β4 nAChR subunits.

Figure 2B:
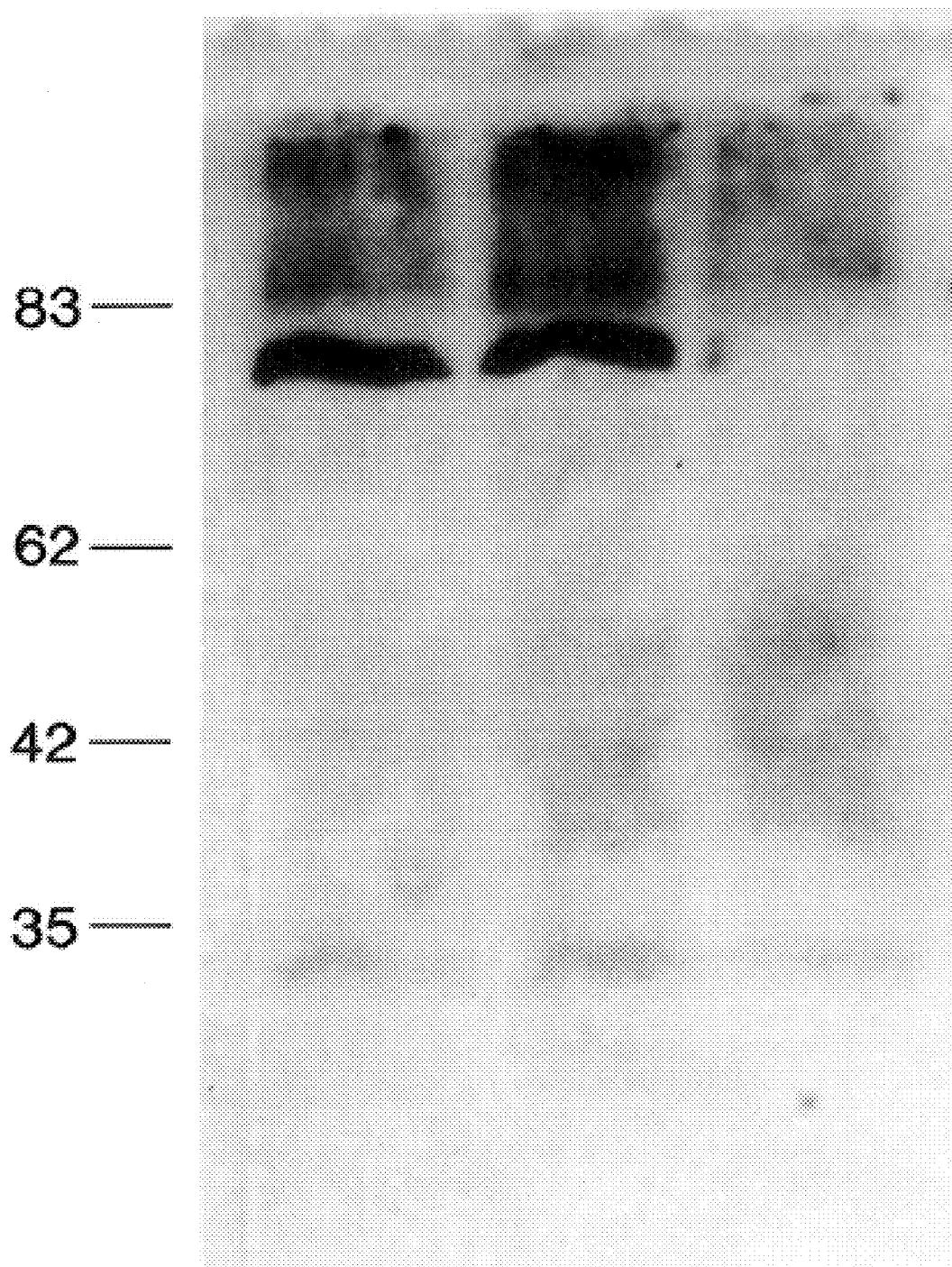
FIG. 2B shows the result of Western blot analysis of total brain protein from +/+,+/-, and -/- mice using a polyclonal antibody raised against a peptide sequence from the α4 subunit.
Figure 3A:
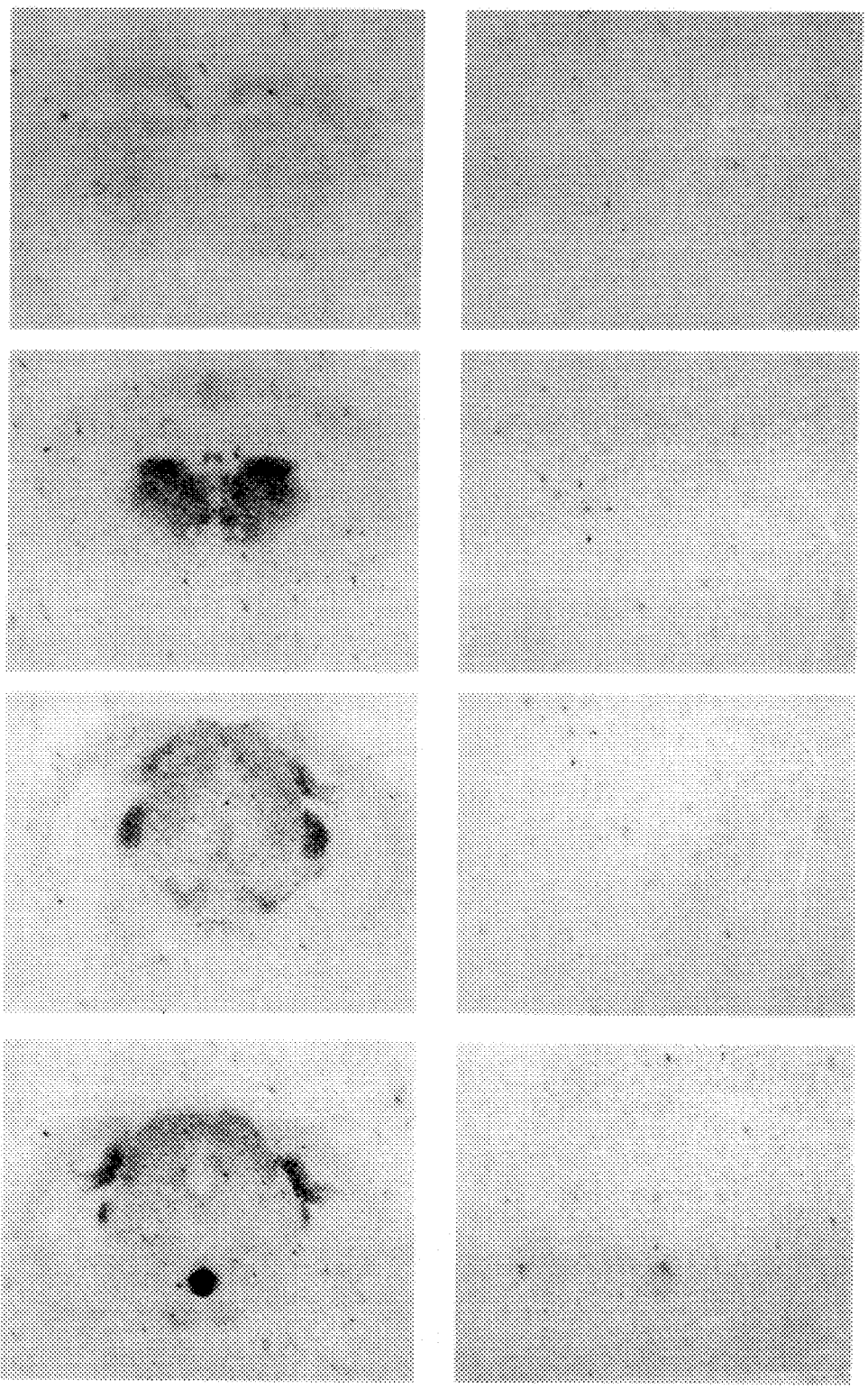
FIG. 3A nicotine.
Figure 3B:
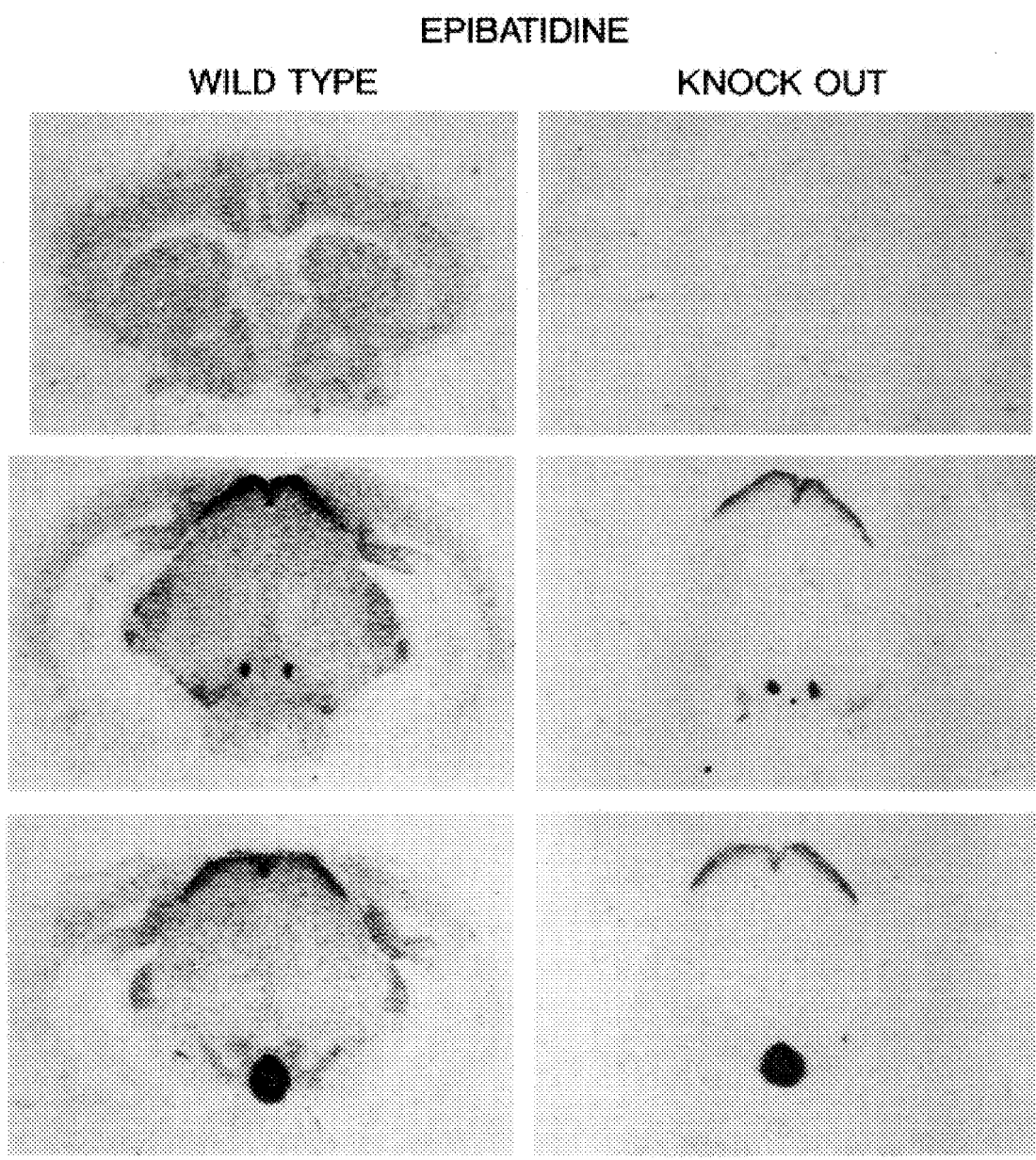
FIG. 3B -epibatidine.
Figure 3C:
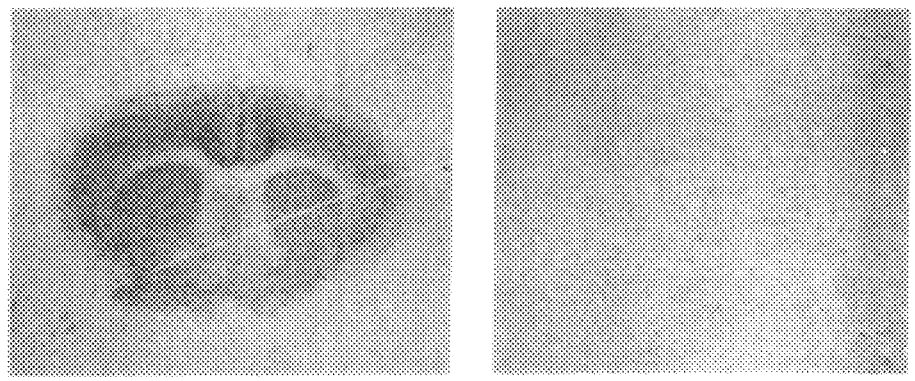
FIG. 3C -cytisine.
Figure 3C:
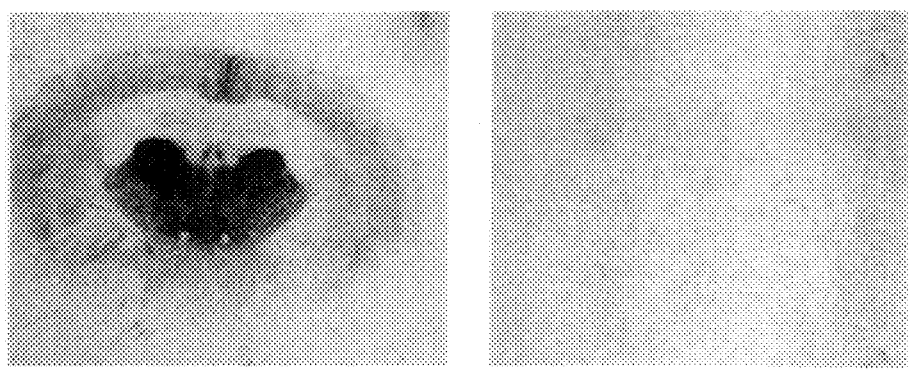
Figure 3C:
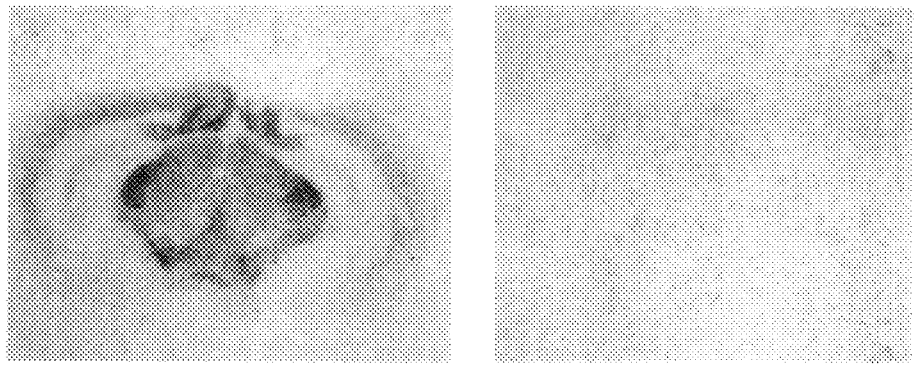
Figure 3C:
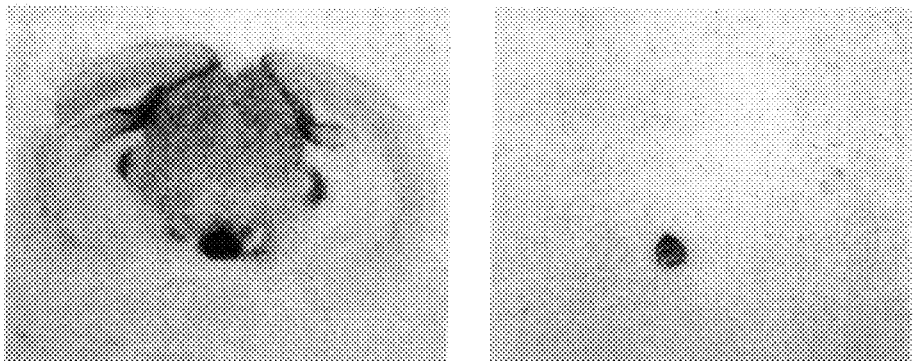

FIG. 2B shows the result of Western blot analysis of total brain protein from +/+, +/–, and –/– mice using a polyclonal antibody raised against a peptide sequence from the α4 subunit. α4-like immunoreactivity is detected in +/+ and +/– mice, but is absent in –/– mice.

In FIG. 3, the results of nicotinic agonist binding in knock-out mice by autoradiography are shown. Mapping of the neuronal nAChR in mouse brain by receptor autoradiograghy using $^3$H-nicotine, $^3$H-epibatidine and $^3$H-cytisine to visualize nAChRs was performed on brain sections from α4 +/+ and –/– mice. Nicotine and cytisine binding was completely abolished except for in the interpeduncular nucleus. In contrast, epibatidine binding was still observed in the medial habenula, the superior colliculus, the substantia nigra, and the interpeduncular nucleus. This indicates that α4 is responsible for almost all of the high affinity nicotine, epibatidine, and cytisine binding sites in the brain. These results are very similar to the ligand-binding profile of the β2 nAChR knockout mice (Zoli et al., Ref. 15), providing some evidence that an α4/β2 receptor complex does occur in vivo and is the receptor subtype responsible for high affinity binding sites.

Figure 4A:
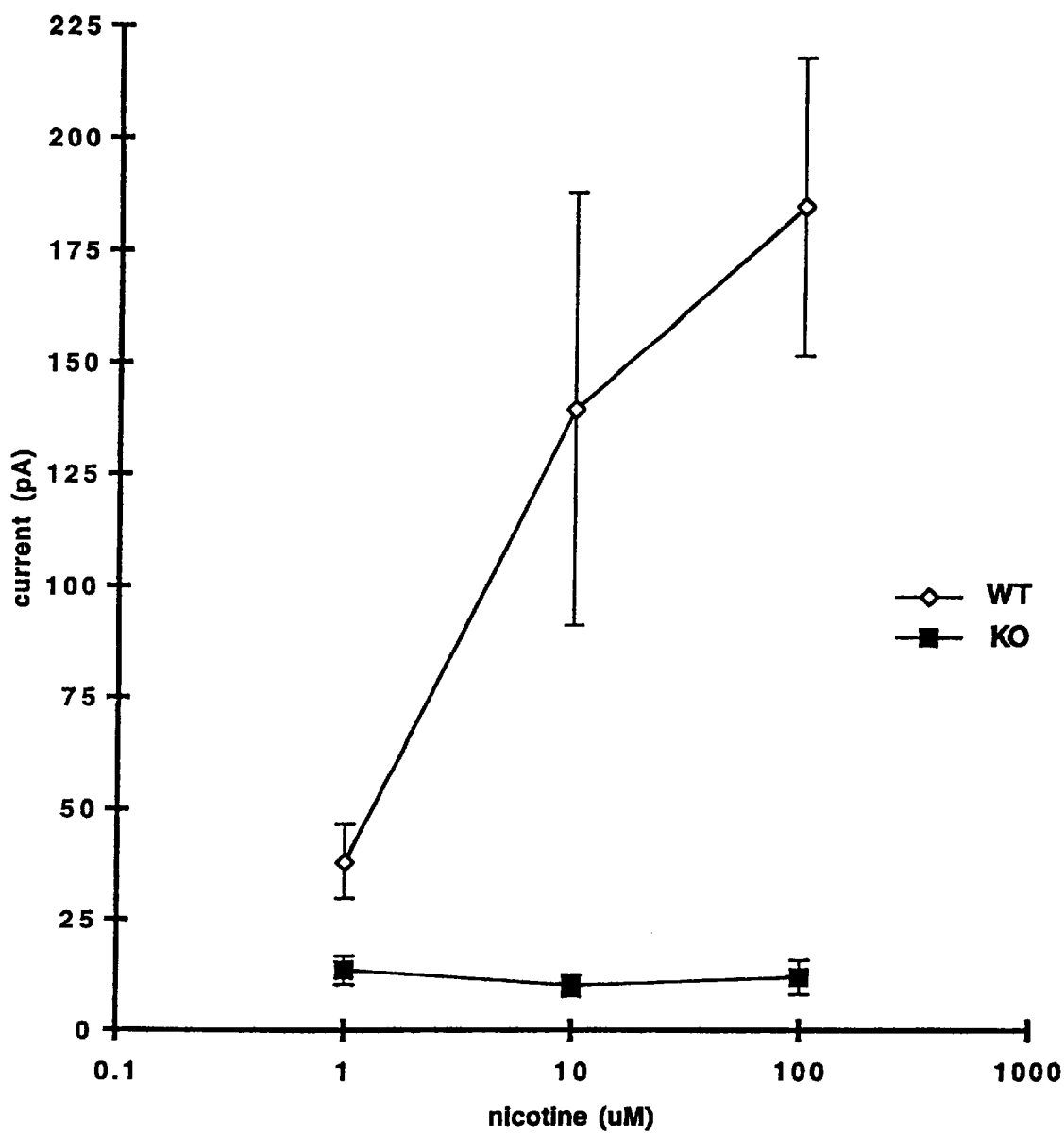
FIG. 4A contains dose response curves of nicotine-evoked currents in the antero-dorsalventro-lateral thalamus (ADVL) of wild type (WT) and mutant mice (KO).

FIG. 4 depicts the results of patch clamp recording in brain slices of knockout mice. FIG. 4A contains dose response curves of nicotine-evoked currents in the anterodorsalventro-lateral thalamus (ADVL) of wild type and mutant mice. The values correspond to mean +/– sem recorded at –60 mV. Each point corresponds to an average of 7 to 8 cells.

Figure 4B:
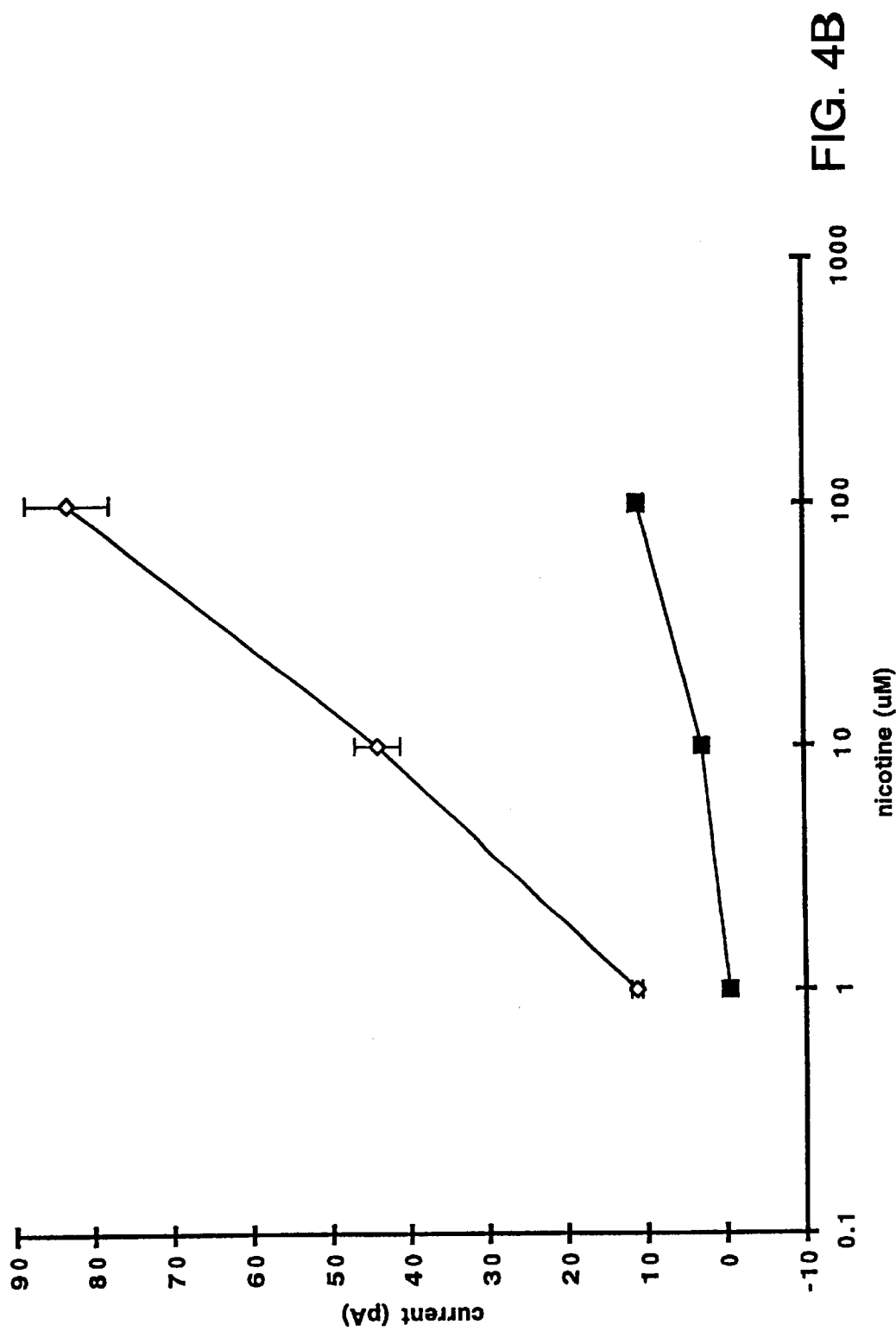
FIG. 4B contains dose response curves of nicotine-evoked currents in the substantia nigra pars compacta (SNC) of wild type and mutant mice.

FIG. 4B contains dose response curves of nicotine-evoked currents in the substantia nigra pars compacta (SNC) of wild type and mutant mice. The values correspond to mean +/– sem recorded at –60 mV. Each point corresponds to an average of 8 cells. FIGS. 4A and 4B show that there is no longer a detectable nicotine elicited current in these cell types in the knock out mice. These data correlate well with the binding experiments in demonstrating that the α4 nAChR subunit is an important functional component of nAChR in the CNS.

Figure 5A:
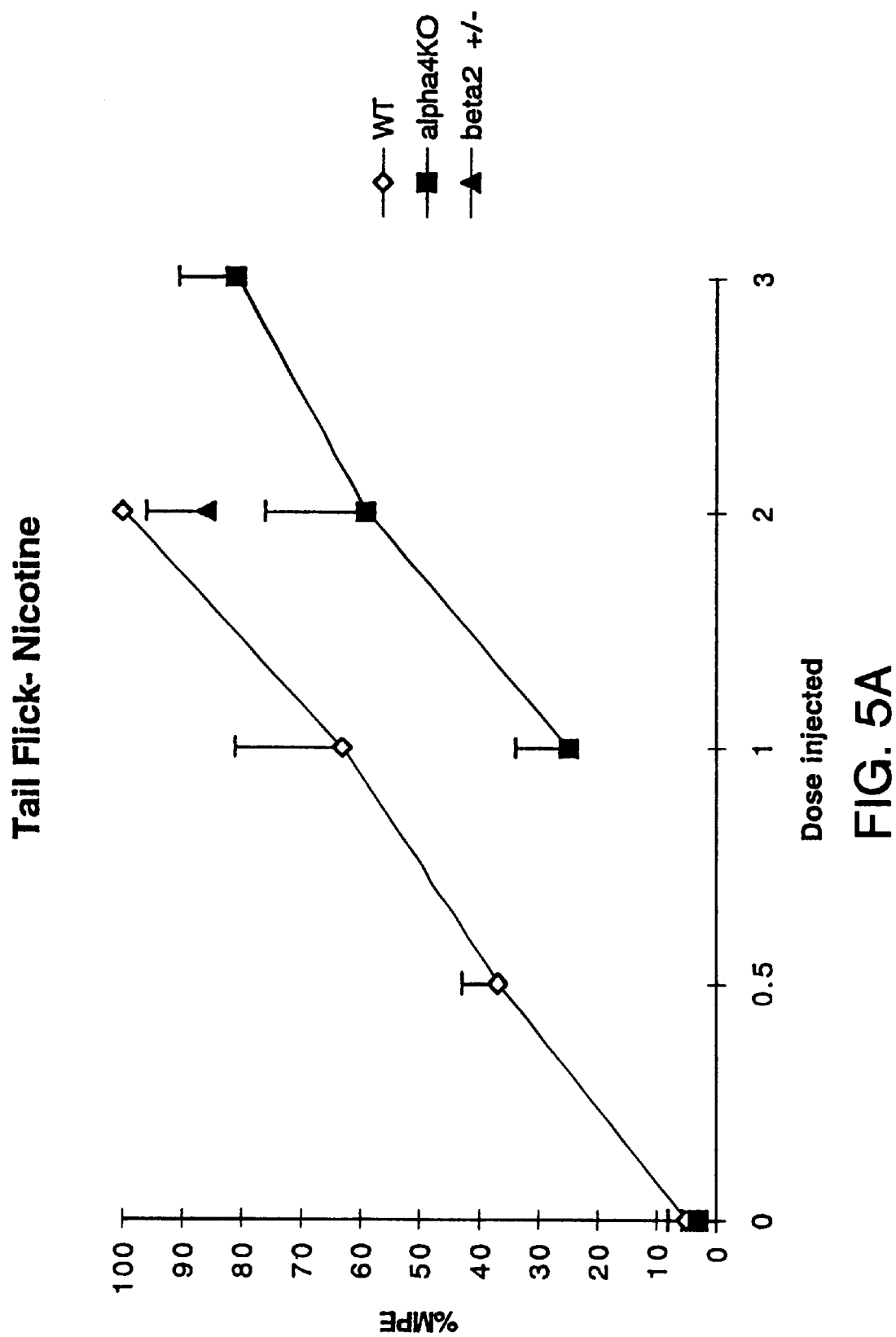
FIG. 5(A–B) depicts the results of nicotine induced analgesia in mutant mice of the invention and wild type mice in the tail-flick test (FIG. 5A) and the hot plate models (FIG. 5B) of analgesia at various doses of nicotine.
Figure 5B:
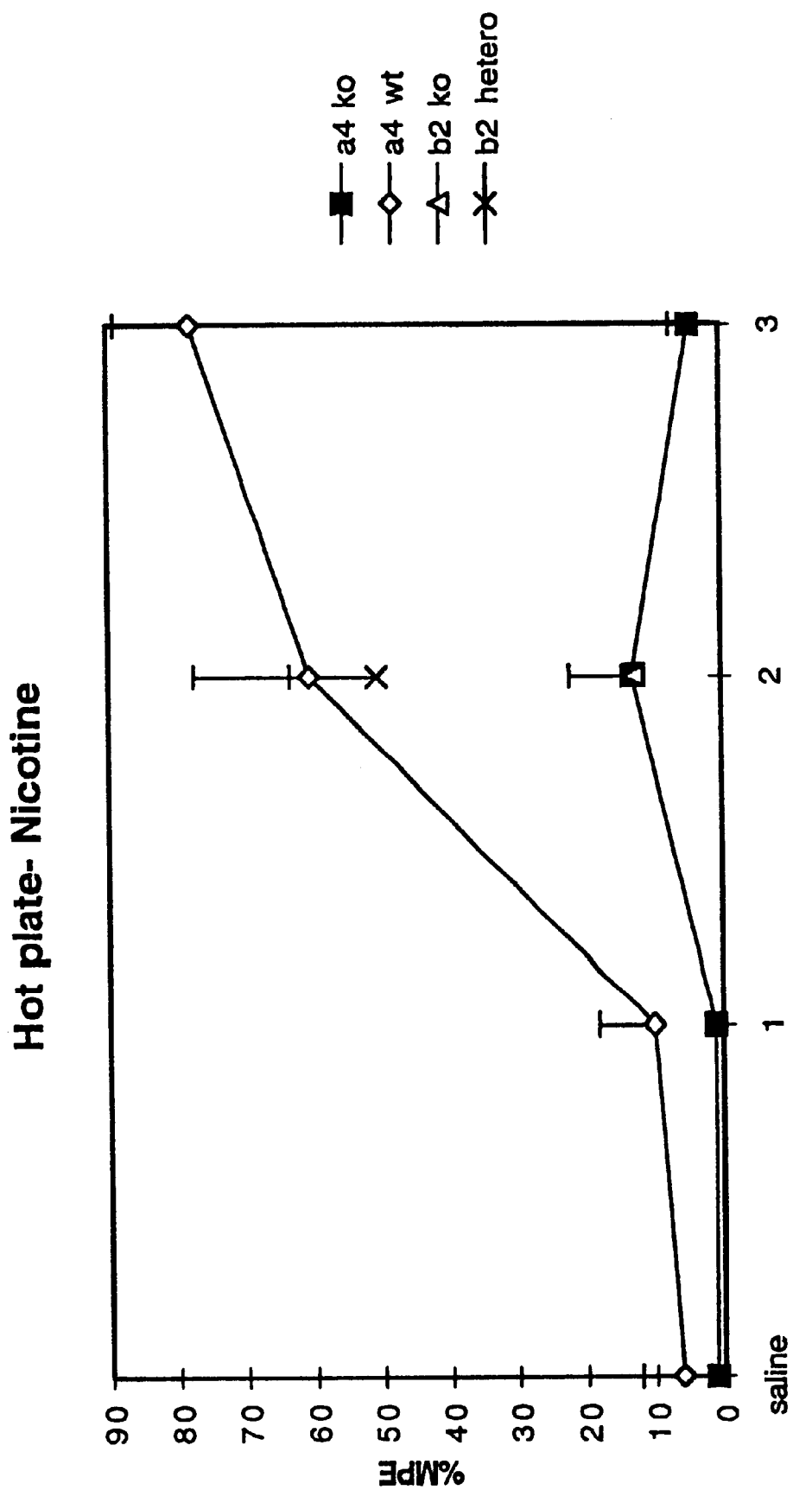

FIG. 5 depicts the results of nicotine induced analgesia in mutant and wild type mice. In FIG. 5A, α4 knockout mice responded to nicotine in the tail-flick test (ED$_{50}$=1.7 mg/kg); however, they were less sensitive than their wild type littermates (ED$_{50}$=0.7 mg/kg). In contrast, with reference to FIG. 5, unlike their wild type littermates, α4 knockout mice did not show signs of nicotine induced analgesia using the hot-plate method even at high doses (up to 3 mg/kg) of nicotine. (Doses given in mg/kg nicotine base).

Figure 6A:
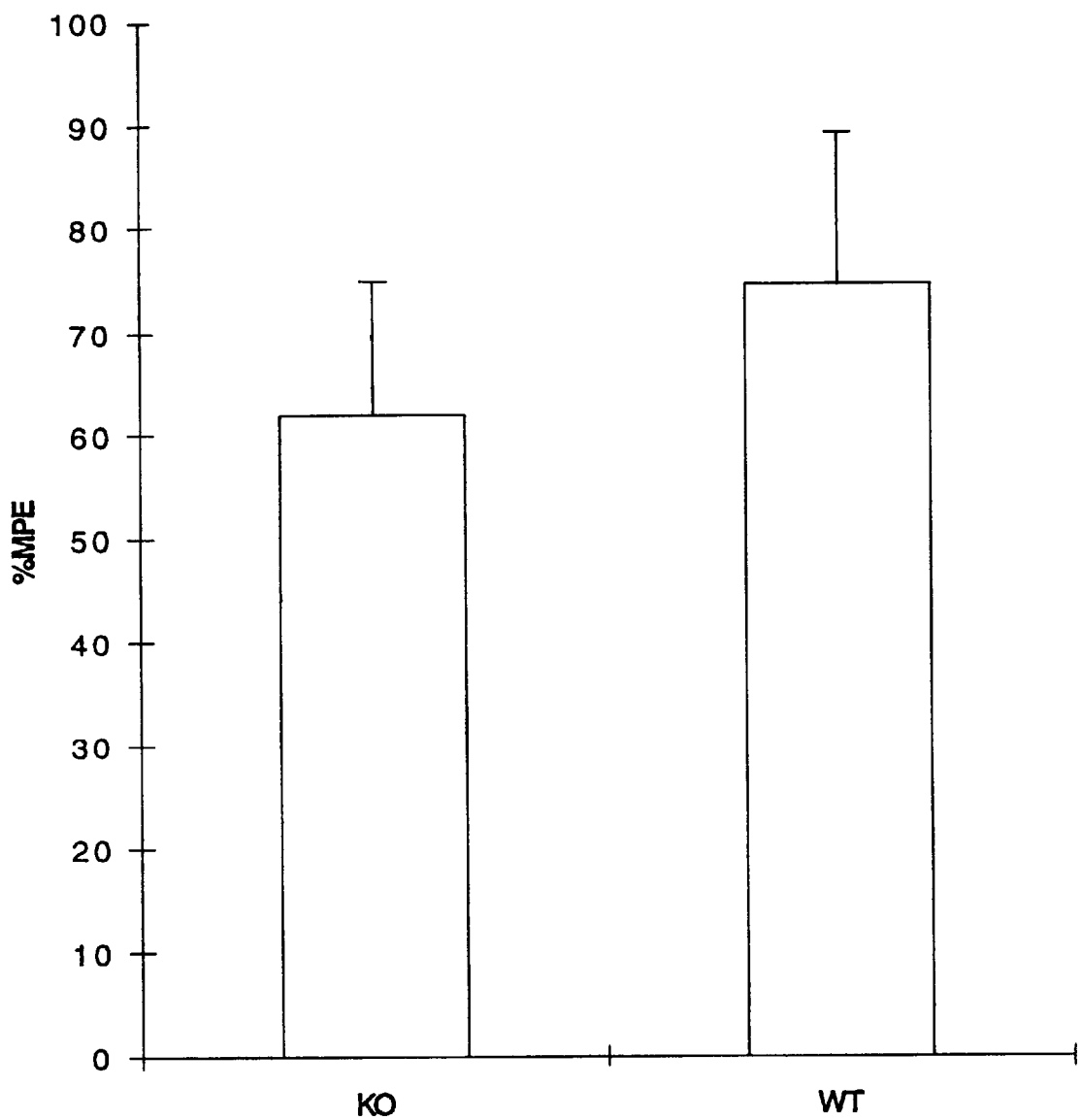
FIG. 6(A–B) shows the results of tests to determine the effects of morphine in mutant mice of the invention and wild type mice in both the hot plate (FIG. 6A) and tail flick (FIG. 6B) models of analgesia.
Figure 6B:
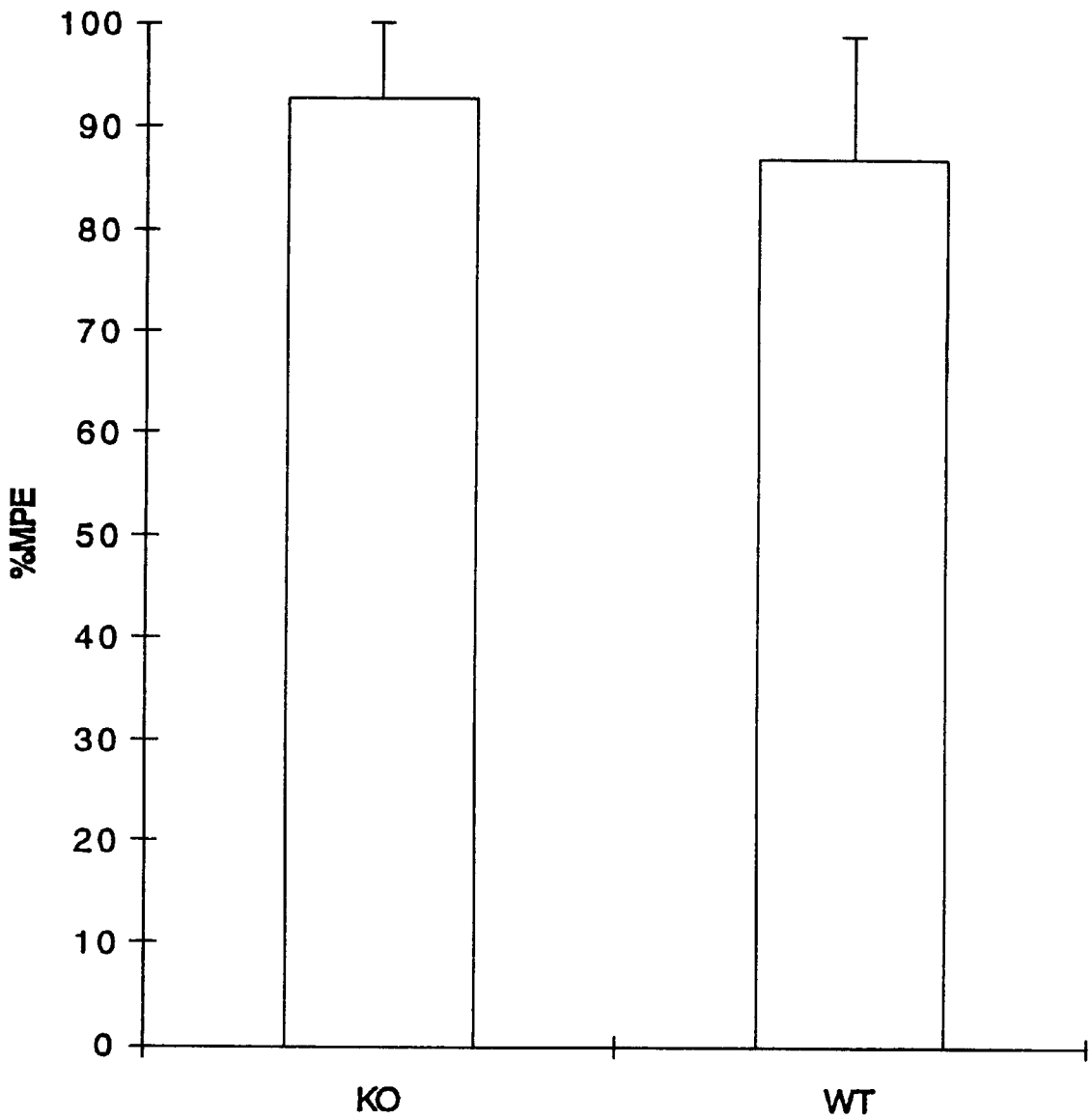

FIG. 6 shows the results of tests to determine the effect of morphine in mutant and wild type mice. Morphine maintained its analgesic effect in both the hot plate and tail flick models of analgesia in both mutant and wild type mice.

Figure 7:
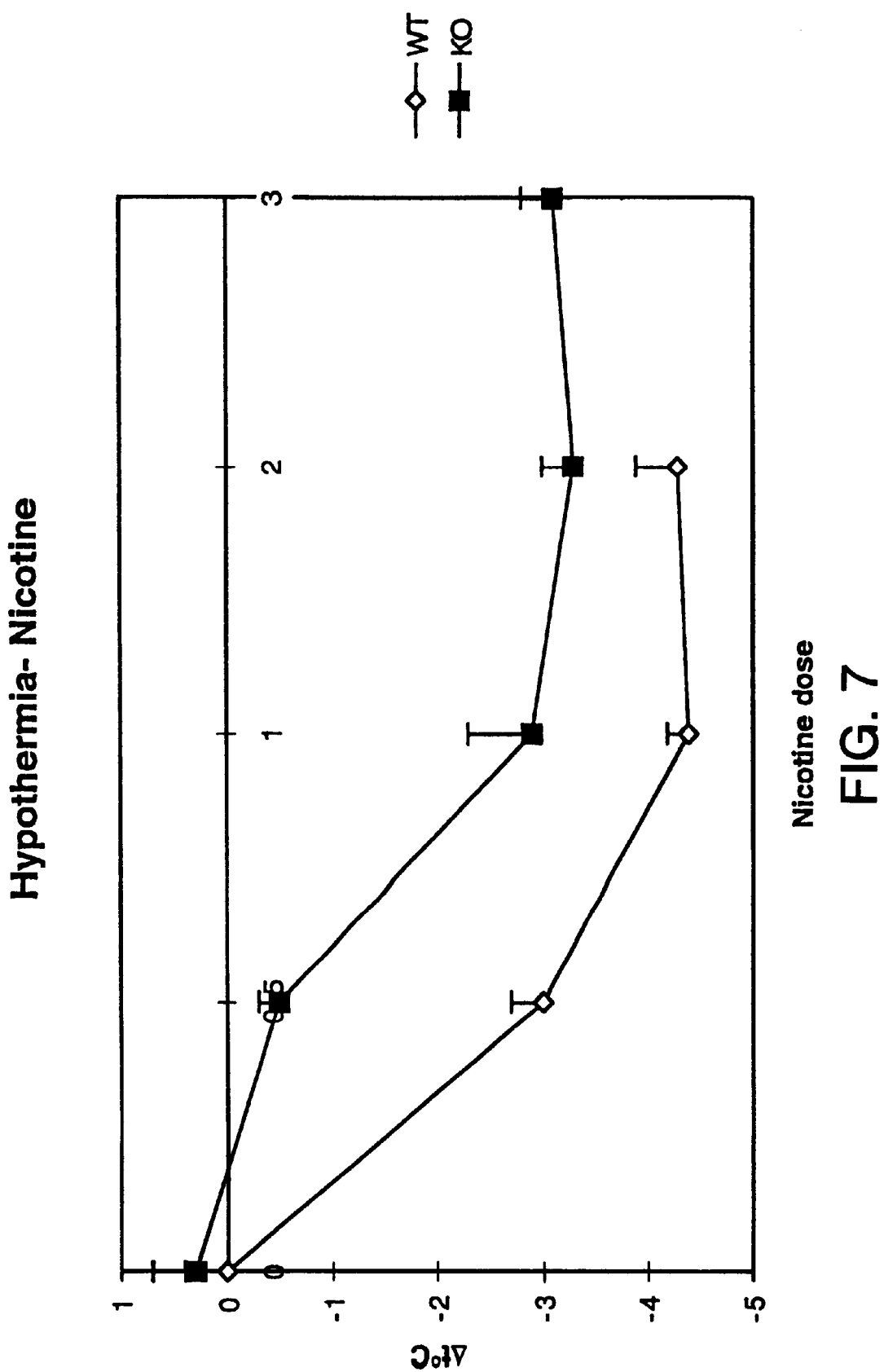
FIG. 7 reports the results of tests to determine nicotine induced hypothermia in mutant mice of the invention and wild type mice.

FIG. 7 reports the results of tests to determine nicotine induced hypothermia in mutant and wild type mice. Nicotine induced hypothermia was present in both wild type and knockout mice; however, knockout mice were less sensitive to nicotine.

Figure 8:
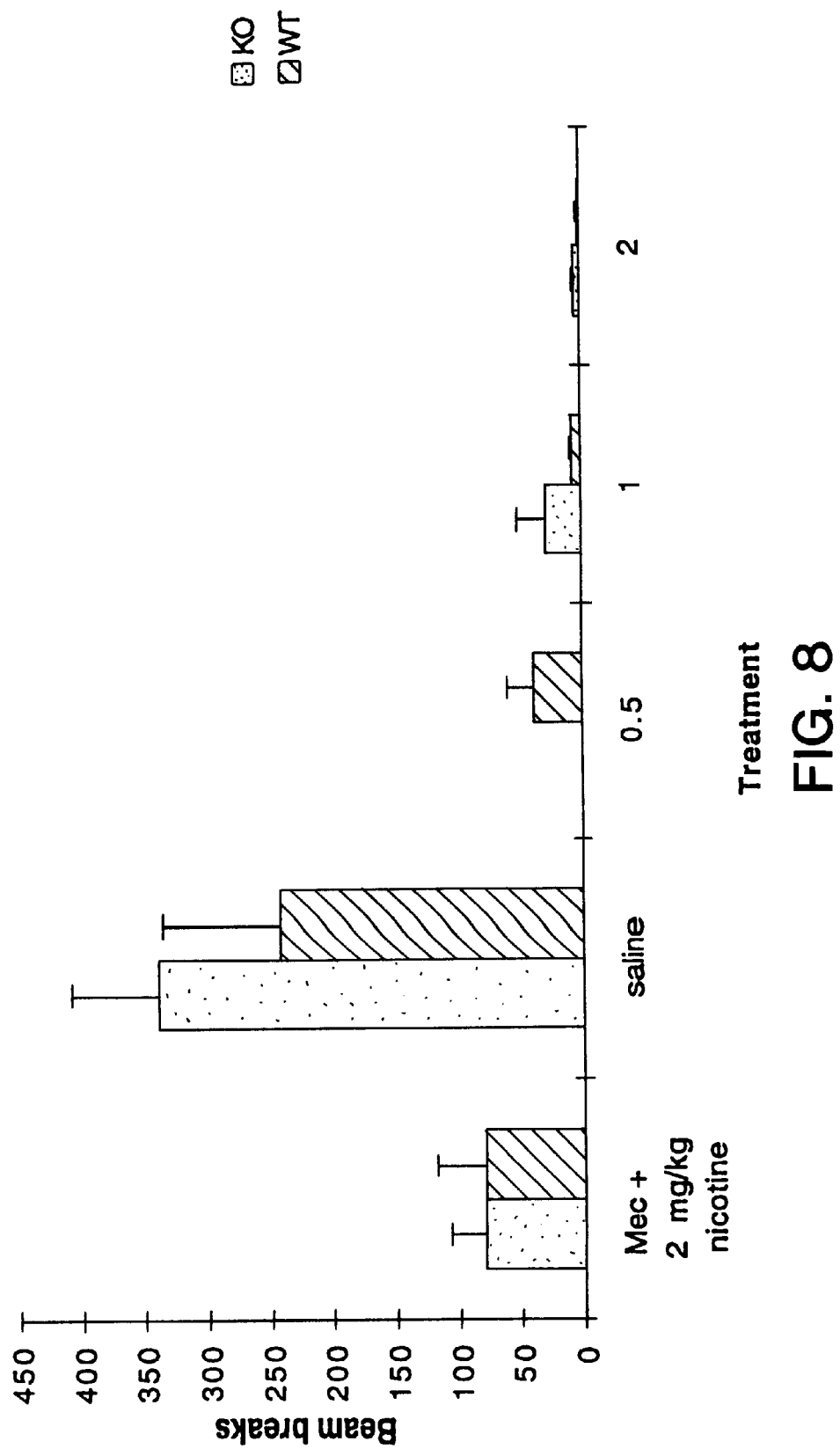
FIG. 8 reports the reduction in non-habituated locomotor activity in the tail flick test.

Finally, FIG. 8 reports the reduction in non-habituated locomotor activity. Nicotine induced reduction of non-habituated locomotor activity occurred in both wild type and mutant mice with no significant difference.

The generation of a mutant line of mice lacking the nicotinic nAChR α4 subunit has been shown here. The comparison of wild type and mutant mice examined the contribution of the α4 subunit in the analgesic effect of nicotine. The mechanisms of nicotine induced analgesia are not very well understood, although it is thought to act through a different pathway than morphine. The results here strongly implicate the α4β2 nAChR in one model of nicotine induced analgesia, the hot plate, or supra-spinal test. In contrast, mutant mice showed only a shift in the dose-response curve in the tail-flick or spinal test. These results clearly separate two different mechanisms of nicotine induced analgesia and implicates the α4 subunit of the nAChR in one of them.

These mice will be useful in assessing the mechanisms of the behavioral effects of nicotine and will aid in identifying specific receptors involved in these behaviors. Moreover, they will be useful in studying and designing nicotinic agonists and other agents, which target certain behaviors while avoiding others.

Techniques useful for obtaining mutant animals of the invention will now be described in greater detail.

Generation of knockout mice:

Exon 5 of the mouse α4 NAChR was cloned by screening a λDASH II male 129 mouse strain genomic library with a full-length rat α4 clone from Jim Heinemann's laboratory, (Jim Heinemann, Molecular Neurobiology Laboratory, The Salk Institute, P.O. Box 85800, San Diego, Calif., U.S.A.,) (clone Hya 23-1E(1)) (Ref. 16). Six over lapping clones were found. Clone 1 was mapped by restriction enzyme digest (FIG. 1). The mouse genomic DNA encoding the exon 5 and 6 of the α4 subunit has been isolated and a DNA construct for homologous recombination has been produced using established methods (Picciotto et al. 1995) [Ref. 8].

In brief, most of exon 5 plus 1 Kb of DNA from the intron sequence upstream from exon 5 was deleted and the neomycin resistant gene was inserted in order to select for cells that have incorporated the DNA construct. In addition, the gene encoding diphtheria toxin (DTA) was inserted 1.3 kB upstream from neo to select against random insertion. DTA will kill any cell that has incorporated the DNA construct without homologous recombination. This construct took advantage of the fact that the upstream region of exon 5 encodes for M1, 2, and 3 transmembrane spanning domains plus the acetylcholine binding site without which a receptor would be completely nonfunctional.

The construct was linearized and transfected into embryonic stem (ES) cells. Colonies surviving after selection with neomycin (Neo) were subcloned and the polymerase chain reaction (PCR) was used to identify homologous recombination versus randomly integrated DNA. Two primers were selected for amplification of ES cell DNA, one in the neomycin resistance gene and the other in a region upstream from the construct sequence. The primers that were used are the following.

5' CAG GAC ATA GCG TTG GCT ACC CGT 3'

Four positive colonies were isolated and injected into mouse blastocysts. Fourteen chimeric mice were born and mated to non-agouti, Black6/C57 males and females. Two of these chimeras were able to pass on the mutant α4 gene as indicated by the color coat marker in approximately 1 out of every 100 of their progeny.

F1 mice were examined by PCR analysis of DNA isolated from the tail to see if they received the mutant α4 gene. One of the four mice was a heterozygote mutant mouse. This F1 female was then crossed with a Black6/C57 male and their F. offspring were interbred to generate homozygote α4 minus mice.

In situ hybridization:

In situ hybridization was as described in ref. 4. Oligonucleotides used are as follows:

```
5' AAA TAG AGT AGA GGC GCC 3'.
```

The oligodeoxynucleotide probes were labeled at the 3' end using a 33P-dATP (NEN) and terminal deoxynucleotidyl transferase (Boehringer, Mannheim) following the specifications of the manufacturer to a specific activity of 200–600 KBq/pmol. The labeled probes were precipitated in ethanol, separated from unincorporated 33P-dATP by means of NucTrap push columns (Stratagene, La Jolla), precipitated again in ethanol, and resuspended in distilled water.

Frozen brains were cut at the cryostat (14 mm thick sections), thaw mounted on Superfrost+slides, and stored at −80° C. (for less than two weeks). The procedure was carried out according to Le Novere et al. 1996. Briefly, sections were fixed with 4% paraformaldehyde for 5 min in room temperature (RT), washed in phosphate buffered saline (PBS), acetylated, and stored in 80% ethanol at 4° C. Sections were then delipidated in ethanol and chloroform (5 min. each), prehybridized for 2–4 h at 37° C. and hybridized for 20 h at 37° C. under parafilm coverslips. The composition of the prehybridization and hybridization mixtures was: 50% formamide, 0.6M NaCl, 10 mM dithiothreitol, 10% dextran sulfate, 1m MEDTA, 1× Denhardt's solution (50×= 1% bovine serum albumin/1% Ficoll/1% polyvinylpyrrolidone), 0.1 mg/ml polyA (Boehringer), 0.5 mg/ml yeast tRNA (Sigma), 0.05 mg/ml herring sperm DNA (Promega) in 0.02M Tris-HCl, pH 7.5. Probes were added in the hybridization mixture at a concentration of 0.55 nM (corresponding to around 15 fmol/section or 3,000–25,000 Bq/30 ml/section according to the labelling).

After the removal of coverslips and an initial rinse in 2× standard saline citrate (SSC) solution (3M NaCl/0.3M sodium citrate) at RT (two times for 5 min), sections were washed three times for 15 min in 1× SSC at RT, for 15 min in 1× SSC at 55° C.

The sections were then rinsed for 15 min in 0.5× SSC at RT. After rinsing in ice-cold water and drying through an alcohol gradient, they were exposed to [3H]Hyperfilm (Amersham) and then to a photographic emulsion (NTB2, Kodak).

Western blot analysis:

Whole extracts from control and α4 mutant mouse brain were homogenized in 5 volumes of boiling lysis buffer (1% SDS, 10 mM Tris-HCl, pH 7.4), and centrifugated at 2200 rpm for 10 min. The supernatant was recollected, aliquoted, and frozen at −80° C. until use. 50 mg aliquots of the samples were separated by sodium dodecyl sulfate-polyacrylamide gel electrophoresis (SDS-PAGE 10% gels). Proteins were transferred to nitrocellulose membranes, which were then blocked overnight with 5% non-fat dry milk in TBST buffer (10 mM Tris-HCl pH 7.5, 100 mM NaCl and 0.1% Tween) at 4° C., and incubated at room temperature with a polyclonal anti-α4 antibody (Santa Cruz Biotechnologies Inc., Calif.) diluted 1:5000 in the same blocking buffer for 1 hour. The membranes were washed with TBST and incubated with a peroxidase conjugated rabbit anti-sheep antibody (Cappel, West Chester, Pa.) diluted 1:5000 for 1 hour, followed by a final washing. Bound peroxidase was detected using enhanced chemiluminescence (ECL, Amersham, England).

Agonist binding:

$^3$H-Nicotine, $^3$H-Epibatidine (Amersham), and $^3$H-Cytisine (NEN) radioactive ligands were used for binding experiments in control and knock-out mice. Animals were decapitated, brains were quickly dissected and frozen in dry ice. 16 mm cryostat sections were cut and mounted on Superfrost/Plus (Menzel-Glaser) slides and stored for not more than two days at −80° C. until use. On the day of experiments, slides were thawed and precessed according to established protocols. Slides were exposed to 3H-Hyperfilm (Amersham) for the length of time indicated and developed in Eastman Kodak D19 film developer.

$^3$H-Nicotine (81 Ci/mmol) was used at a concentration of 4nM. The incubation was carried out at room temperature for 30 min in 50 mM Tris HCl pH 7.4 and 8 mM $CaCl_2$, followed by two rinses of 2 min in 50 mM Tris-HCl pH 7.4 and a brief rinse in distilled water, all at 4° C. Non-specific binding was defined as the binding in the presence of cold nicotine (10 mM) (Data not shown). The film was exposed for 3 months.

$^3$H-Epibatidine (53 Ci/mmol) was used at a concentration of 200 pM. The incubation was carried out at room temperature for 30 min in 50 mMTris HCl pH 7.4. It was followed by two rinses of 5 min in the same buffer followed by a brief rinse in distilled water, all carried out at 4° C. Non-specific binding was defined as the binding in the presence of cold nicotine (10 mM) (Data not shown). The film was exposed for 24 days.

3H-Cytisine (32 Ci/mmol) was used at a concentration of 2 nM. The incubation was carried out at 4° C. for 60 min in 50 mM Tris HCl pH 7.4. It was followed by two rinses of 2 min in the same buffer followed by a brief rinse in distilled water, all carried out at 4° C. Non-specific binding was defined as the binding in the presence of cold nicotine (10 mM) (Data not shown). The film was exposed for 45 days.

Antinociceptive assays:

Antinociception was assessed by the tail-flick method of D'Amour and Smith (1941, J. Pharmacol. Exp. Ther.; 72:74–79). A AWOFFICES control response (2–6 sec) was determined for each animal before treatment, and a test latency was determined after drug administration. To minimize tissue damage, a maximum latency of 10 sec was imposed. Antinociceptive response was calculated as % MPE, where % MPE=[(test-control)/(10-control)]×100.

Groups of 6 to 12 animals were used for each dose and for each treatment. The mice were tested 5 min after subcutaneous injections of nicotinic ligands for the dose-response evaluation. Antagonism studies were carried out by pretreating the mice s.c. with the nicotinic antagonist, mecamylamine, 10 min before nicotine. The animals were tested 5 min. after administration of the agonist.

Animals were retested using the hot plate method one week later to allow any residual nicotine to clear out of the system. A glass container 11 cm in diameter and 13 cm high restricted the animal to the middle of a 55° C. hotplate. A control response (4–8 sec) was determined for each animal before treatment. The nociceptive endpoints in the hotplate test were paw-licking or jumping. The maximum cut-off time for this test was 20 sec.

The mice were tested 5 min after subcutaneous injections of nicotinic ligands for the dose-response evaluation. Antinociceptive response was calculated as % MPE, where % MPE=[(test-control)/(20-control)]×100. Antagonism studies were carried out by pretreating the mice s.c. with mecamylamine 10 min before nicotine. The animals were tested 5 min. after administration of the agonist.

Locomotor activity:

After the tail flick assay, most mice were tested for locomotor activity. Mice were placed into individual photocell activity cages (28×16.5 cm) about 6 minutes after s.c.

administration of either 0.9% saline or nicotine (0.5, 1, or 2 mg/kg). Interruptions of the photocell beams (two banks of eight cells each) were then recorded for the next 10 min. Data were expressed as total number of photocell interruptions.

For antagonism studies, the mice were pretreated s.c. with mecamylamine 10 min before nicotine.

Body Temperature:

Rectal temperature was measured by a digital thermometer (inserted 24 mm) (Yellow Springs Instrument Co., Yellow Springs, Ohio). Readings were taken just before and 20 min after the s.c. injection of nicotine. For antagonism studies, mice were pretreated with mecamylamine (s.c.) 10 min before nicotine. The difference in rectal temperature before and after treatment was calculated for each mouse.

As discussed above, the experimental results described herein have demonstrated that knockout mice lack functional α4 subunits of the nAChR. Based on this discovery, a screening procedure has been developed for identifying therapeutic compounds that affect nicotine activity in vivo. In general, the method involves screening any number of compounds for therapeutically active agents by employing the mutant and transgenic animals described herein. Based on the above results, it will be readily understood that a compound that alters nicotine activity in an animal (e.g., the mutant mouse described herein) can provide an effective therapeutic agent in a mammal (e.g., a human patient). Since the screening procedures of the invention are performed in vivo, it can be ascertained whether candidate compounds will be highly toxic to a mammalian host organism (e.g., a human patient). In addition, the invention also makes available high throughput in vitro screening methods for the screening of large quantities of candidate compounds using the cells and cell lines of the invention.

Accordingly, the methods, materials, and animals of the invention simplify the evaluation, identification, and development of active agents, such as drugs, for the treatment of a variety of diseases. In general, the screening methods of the invention provide a facile means for selecting any number of compounds of interest from a large population that are further evaluated and condensed to a few active and selective materials. Constituents of this pool can then be evaluated in the methods of the invention to determine their activity.

Administration of the candidate compound to a mouse of the invention can be by any known route, e.g., intraperitoneally, and at a range of concentrations. Following an appropriate period of time, the animal can be assessed for the effect of the compound compared to control animals.

Cells from the transgenic animals of the invention are also useful as a source of cells for cell culture, and for the preparation of cell membranes that are useful for analyzing the effects of candidate agonists on nAChR activity.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

REFERENCES

The following publications have been cited herein. The entire disclosure of each publication is relied upon and incorporated by reference herein.

1. Sargent, P. B. *Annu. Rev. Neurosci.* 16, 403–443 (1993).
2. McGehee, D. S. & Role, L. W. *Annu. Rev. Physiol.* 57, 521–546 (1995).
3. Bertrand, D., & Changeux, J. P. *Semin. Neurosci.* 7, 75–90 (1995).
4. Duvoisin, R., Deneris, E., Patrick, J. & Heinemann, S. Neuron 3, 487–496 (1989).
5. Zoli, M., LeNov re, N., Hill, J. A. J. & Changeux, J. P. *J. Neurosci.* 15, 1912–1939 (1995).
6. Flores, C. M., Rogers, S. W., Pabreza, L. A., Wolfe, B. B. & Keller, K. *Mol. Pharmacol.* 41, 31–37 (1992).
7. Luetje, C. W. & Patrick, *J. J. Neurosci.* 11, 837–845 (1991).
8. Picciotto, M., et al. *Nature* 374, 65–67 (1995).
9. LeNovere, N. & Changeux, J. P. *J. Mol. Evol.* 40, 155–172 (1995).
10. Levin, E. D. *Psychopharmacology* 108, 417–431 (1992).
11. Tripathi, H. L., Martin, B. R. & Aceto, M. D. *J. Pharm. Exp. Therap.* 221, 91–96 (1982).
12. Brioni, J., O'Neill, A., Kim, D., Buckley, M. & Decker, M. W. *Eur. J. Pharmacol.* 238 (1993).
13. Steinlein, O. K., A. Magnusson, J. Stoodt, S. Bertrand, S. Weiland, S. F. Berkovic, K. O. Nakken, P. Propping, and D. Bertrand, "An insertion mutation of the CHRNA4 gene in a family with autosomal dominant nocturnal frontal lobe epilepsy." *Human Molecular Genetics* 6 (6 1997): 943–947.
14. Steinlein, O. K., J. C. Mulley, P. Propping, R. H. Wallace, H. A. Phillips, G. R. Sutherland. I. E. Scheffer, and S. F. Berkovic, "A missense mutation in the neuronal nicotinic acetylcholine receptor α4 subunit is associated with autosomal dominant nocturnal frontal lobe epilepsy." *Nature Genetics* 11 (1995): 201–204.
15. Zoli, M., C. Lena, M. R. Picciotto, and J. P. Changeux, "Identification of Four Classes of Brain Nicotinic Receptors Using Beta-2 Mutant Mice." *Journal of Neuroscience* 18 (12 1998): 4461–4472.
16. Goldman, D., Deneris, E., Luyten, W., Kochar, A., Patrick, J. and Heinemann, S. "Members of a nicotinic acetylcholine receptor gene family are expressed in different regions of the mammalian central nervous system. *Cell* 48: 965–973 (1987).

What is claimed is:

1. A transgenic mouse whose genome comprises a homozygous disruption of the α4 subunit of the endogenous nicotinic acetylcholine receptor (nAChR) gene, wherein said disruption comprises the insertion of a transgene, and wherein said disruption results in said transgenic mouse not exhibiting nicotine induced antinociception upon exposure to nicotine.

2. The transgenic mouse of claim 1, wherein the homozygous disruption of the nAChR gene results in a reduction in nicotine, cytisine, or epibatidine binding sites in the brain of said transgenic mouse as compared to a wild-type mouse.

3. The transgenic mouse of claim 1, wherein the transgene comprises a nucleotide sequence that encodes a selectable marker.

4. A method of screening for a compound that is an agonist or antagonist of nicotine, comprising:
   A) exposing the transgenic mouse of claim 1 to said compound;
   B) administering nicotine to said transgenic mouse prior to, after, or simultaneously with step A; and
   C) determining the response of said transgenic mouse to nicotine, wherein a change in response compared to a transgenic mouse of claim 1 not exposed to said compound, indicates the effect of said compound on nicotinic activity.

5. The method of claim 4, wherein response to the compound is determined by the tail-flick method, the hot plate method, or nicotine induced hypothermia.

6. A DNA knockout construct comprising a DNA sequence encoding a selectable marker, wherein said DNA sequence encoding a selectable marker is flanked by DNA sequences homologous to the α4 subunit gene of the mouse nicotinic acetylcholine receptor (nAChR), and wherein said DNA sequence encoding a selectable marker replaces the first 900 nucleotides of exon 5 of the α4 subunit gene.

7. A vector comprising the DNA knockout construct of claim 6.

* * * * *

UNITED STATES PATENT AND TRADEMARK OFFICE
CERTIFICATE OF CORRECTION

PATENT NO.   : 6,252,132 B1
DATED        : June 26, 2001
INVENTOR(S)  : Changeux et al.

It is certified that error appears in the above-identified patent and that said Letters Patent is hereby corrected as shown below:

<u>Title page,</u>
Item [75], please change "[75] Inventors: Jean-Pierre Changeux; Lisa Marubio, both of Paris (FR)" to -- [75] Inventors: Jean-Pierre Changeux; Lisa Marubio, both of Paris, (FR); Imad Damaj of Richmond, VA (USA); and Steven Brown of Stockholm (SW) --.

Signed and Sealed this

Fifteenth Day of July, 2003

JAMES E. ROGAN
*Director of the United States Patent and Trademark Office*